United States Patent
Tanaka et al.

(10) Patent No.: US 10,048,216 B2
(45) Date of Patent: Aug. 14, 2018

(54) X-RAY ANALYZER

(71) Applicant: HITACHI HIGH-TECH SCIENCE CORPORATION, Minato-ku, Tokyo (JP)

(72) Inventors: Keiichi Tanaka, Tokyo (JP); Kazuo Chinone, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 104 days.

(21) Appl. No.: 15/016,362

(22) Filed: Feb. 5, 2016

(65) Prior Publication Data

US 2016/0231259 A1    Aug. 11, 2016

(30) Foreign Application Priority Data

Feb. 5, 2015 (JP) .................................. 2015-021592

(51) Int. Cl.
| | |
|---|---|
| *G01N 23/223* | (2006.01) |
| *G01N 23/2252* | (2018.01) |
| *H01L 39/10* | (2006.01) |
| *H01L 39/16* | (2006.01) |

(52) U.S. Cl.
CPC ......... *G01N 23/2252* (2013.01); *H01L 39/10* (2013.01); *H01L 39/16* (2013.01); *G01N 2223/3103* (2013.01)

(58) Field of Classification Search
CPC ........ G01N 23/00; G01N 23/223; A61B 6/06; A61B 6/485; G21K 1/02; H01J 5/18; H01J 35/18

USPC .................................. 378/44, 147, 156, 161
See application file for complete search history.

(56) References Cited

U.S. PATENT DOCUMENTS

2009/0184252 A1    7/2009 Tanaka et al. ........... 250/370.09

OTHER PUBLICATIONS

Extended European Search Report dated Jun. 8, 2016 in European Patent Application No. 16154231.1.
Wollman D A et al: "High-resolution, energy-dispersive microcalorimeter spectrometer for X-ray microanalysis", Journal of Microscopy, Blackwell Science, GB, vol. 188, Dec. 1, 1997 (Dec. 1, 1997), pp. 196-223.
M.R.J. Palosaari et al: "Transition-Edge Sensors for Particle Induced X-ray Emission Measurements", Journal of Low Temperature Physics., vol. 176, No. 3-4, Dec. 15, 2013 (Dec. 15, 2013), pp. 285-290.

(Continued)

*Primary Examiner* — Jurie Yun
(74) *Attorney, Agent, or Firm* — Adams & Wilks (57) ABSTRACT

An X-ray analyzer includes: an excitation source for exciting a sample to radiate a characteristic X-ray; an X-ray detector that detects the characteristic X-ray; a collimator; at least one window that is provided between the sample and the X-ray detector and allows the characteristic X-ray to pass through; and a cooling unit that cools the window, wherein the window is laminated with one or more layer of an aluminum film and one or more layer of an insulating film, wherein a total thickness of the aluminum film of the at least one window is equal to or greater than 150 nm and is less than 300 nm, and wherein a size of the collimator is set such that a quantity of radiant heat to the X-ray detector of the atmospheric temperature when the window is not present is equal to or less than 10 μW.

9 Claims, 8 Drawing Sheets

(56) References Cited

OTHER PUBLICATIONS

Keiichi Tanaka et al: "A microcalorimeter EDS system suitable for low acceleration voltage analysis", Surface and Interface Analysis., vol. 38, No. 12-13, Dec. 1, 2006 (Dec. 1, 2006), pp. 1646-1649.
"Transition Edge Sensor-Energy Dispersive Spectrometer (TES-EDS) and Its Applications" Keiichi Tanaka, et al., IEICE Transactions on Electronics, vol. E92-C, No. 3, 2009, p. 334-340.
AP X-Ray Windows, [online]. MOXTEK Incorporated, 2010. [retrieved on Jan. 19, 2015]. Retrieved from the Internet URL:http://moxtek.com/xray-product/ap-windows.

X-RAY ANALYZER

CROSS-REFERENCE TO RELATED APPLICATION

This application claims priority from Japanese Patent Application No. 2015-021592, filed on Feb. 5, 2015, the entire subject matter of which is incorporated herein by reference.

BACKGROUND

1. Field of the Invention

The present invention relates to an X-ray analyzer provided with a radiation detector including a superconducting transition edge sensor.

2. Description of the Related Art

As an X-ray analyzer capable of discriminating X-ray energy, there are energy dispersive spectroscopy (hereinafter, referred to as EDS) and wavelength dispersive spectroscopy (hereinafter, referred to as WDS).

The EDS is an X-ray detector for converting X-ray energy input to the detector into an electrical signal and calculating energy according to the level of the electrical signal. The WDS is an X-ray detector for making an X-ray monochromatic (energy discrimination) using X-ray spectroscopy and detecting the monochromatic X-ray using a proportional counter tube or the like.

As the EDS, a semiconductor detector such as an SiLi (silicon lithium) type detector, a silicon drift type detector or a germanium detector is known. For example, a silicon lithium type or silicon drift type detector is widely used for an element analyzer of an electron microscope to detect energy in a wide range of about 0.2 keV to 20 keV. However, since silicon is used in the detector, in principle, the property of the detector depends on the band gap (about 1.1 eV) of silicon, it is difficult to improve energy resolution to about 130 eV or more, and energy resolution is lower than that of the WDS by 10 times or more.

Energy resolution, which is an index indicating performance of the X-ray detector, of, for example, 130 eV means that, when X-ray is irradiated to the X-ray detector, energy may be detected with uncertainty of about 130 eV. Accordingly, as uncertainty decreases, energy resolution increases. That is, if a characteristic X-ray composed of two adjacent spectrums is detected, uncertainty decreases as energy resolution increases. When a difference in energy between two adjacent peaks is about 20 eV, in principle, the two peaks may be divided with energy resolution of about 20 eV to 30 eV.

Recently, an energy dispersive superconducting X-ray detector having the same energy resolution as the WDS has been attracting attention. Among superconducting X-ray detectors, a detector having a superconducting transition edge sensor (hereinafter, referred to as a TES) is a high-sensitivity calorimeter using rapid resistance change (e.g., temperature change is several mK and resistance change is 0.1 Ω) upon superconduction-normal conduction transition of a metal thin film. In addition, this TES is referred to as a micro calorimeter.

A sensitive area in which a TES may detect an X-ray is in an intermediate area of normal conduction and superconduction and this point is referred to as an operation point. In order to maintain the TES at this operation point, heat balance of Joule heat generated within the TES and heat escaping from the TES to a heat tank via a heat link is formed. This heat balance is expressed as shown in Equation (1) by current I flowing in the TES, operation resistance R of the TES, heat conductivity G of the heat link, the temperature T of the TES, the temperature Tb of the heat tank and the heat Pex intruded from outside. The heat Pex intruded from outside is ideally zero.

$$IR^2 + P_{ex} = G(T - T_b) \quad (1)$$

This TES analyzes a sample by detecting temperature change in the TES occurring when a fluorescent X-ray or characteristic X-ray generated from the sample by irradiation of radiation such as a primary X-ray or a primary electron beam is made incident. The TES has energy resolution higher than the other detectors and may obtain energy resolution of 10 eV or less in the characteristic X-ray of 5.9 keV, for example.

When the TES is attached to a scanning electron microscope or a transmission electron microscope, by obtaining the characteristic X-ray generated from the sample, to which an electron beam is irradiated, is obtained by the TES, the peaks of the energy spectrums of the characteristic X-ray (for example, Si-Kα, W-Mα, W-Mβ, or the like), which cannot be divided by the semiconductor type X-ray detector, can be easily divided.

The TES is a high-sensitivity calorimeter and thus requires a plurality of heat shields, for stable operation. However, since the X-ray generated from the sample need to be introduced to the TES, an X-ray window is mounted in the heat shield (see Related-Art Document 1 listed below). In the configuration disclosed in the Related-Art Document 1, X-ray windows are mounted in heat shields respectively cooled to 4K and 80K. The X-ray windows pass the X-ray to be analyzed but block visible light or infrared light which causes noise.

In addition to the heat shields, in order to form the TES as one vacuum chamber, the X-ray window having vacuum resistance is formed to shield the outer atmosphere of a room temperature. In general, as the X-ray window having vacuum resistance, an X-ray window using an organic film is used (see Related-Art Document 2 listed below). When three X-ray windows are mounted, transmittance of X-ray is significantly reduced to 60% (1 keV) to 1% (0.2 keV or less).

Related-Art Document 1: "Transition Edge Sensor-Energy Dispersive Spectrometer (TES-EDS) and Its Applications" Keiichi TANAKA, et al., IEICE TRANSACTIONS on Electronics, vol. E92-C No.3, 2009, p.334-340

Related-Art Document 2: AP X-ray Windows. [online] . MOXTEK Incorporated, 2010. [retrieved on 2015-01-19]. Retrieved from the Internet URL: http://moxtek.com/xray-product/ap-windows

SUMMARY

The present disclosure has been made in view of the above-described circumstances, and one of the objects of the present disclosure is to provide an X-ray analyzer capable of shielding heat intruded from outside, such as blackbody radiation, and reducing the thickness of an X-ray window to the minimum to efficiently acquire an X-ray of 1 key or less.

According to an exemplary embodiment of the present disclosure, there is provided an X-ray analyzer including: an excitation source for exciting a sample to be analyzed to radiate a characteristic X-ray; an X-ray detector that detects the characteristic X-ray; a collimator that regulates a range of the characteristic X-ray incident to the X-ray detector; at least one window that is provided between the sample and the X-ray detector and allows the characteristic X-ray to pass through; and a cooling unit that cools the window to a temperature that is lower than an atmospheric temperature. The window is laminated with one or more layers of an aluminum film and one or more layers of an insulating film. A total thickness of the aluminum film of the at least one window is equal to or greater than 150 nm and is less than 300 nm. A size of the collimator is set such that a quantity of radiant heat to the X-ray detector of the atmospheric temperature when the window is not present is equal to or less than 10 μW.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

In a conventional X-ray analyzer having TES, X-ray transmission efficiency of 1 keV or less may not be satisfactory and, for example, detection efficiency of boron (183 eV) is worse than that of the existing silicon drift detector (hereinafter, referred to as an SDD) by one digit. This is because the SDD requires only one X-ray window using an organic film while the TES requires two or more X-ray windows for heat shield in addition to an X-ray window using an organic film.

The TES has an operation temperature lower than that of the SDD and X-ray windows greater in number than the number of X-ray windows in the SDD need to be formed as the heat shield in order to stably operate the TES. Therefore, it is necessary to stably operate the TES while increasing acquisition efficiency of a characteristic X-ray of 1 kV or less.

In order to improve transmission efficiency of the X-ray, it is preferable to set the thickness of the window as small as possible. However, in order to stably operate the TES, blackbody radiation from the room temperature needs to be sufficiently considered. Since blackbody radiation is proportional to the fourth power of the temperature, if the thickness of the X-ray window is excessively small, blackbody radiation of the room temperature is not all absorbed into the X-ray window but penetrates the X-ray window, and is absorbed into the TES, such that operation of the TES becomes unstable. The TES needs to be always maintained at the constant operation point (that is, current flowing in the TES is constant), but, as shown in Equation (1), when heat Pex intruded from outside increases, although the self-Joule heat $IR^2$ is small, heat Pex intruded from outside and heat from the TES to the heat tank balance.

When heat is intruded from outside, current flowing in the TES is changed to deteriorate energy resolution. In order to stably operate the TES, current of the TES needs to be made constant such that heat is designed so as to ignore influence of heat Pex intruded from outside.

In order to achieve the object, the present disclosure proposes the following aspects of the present invention.

(1) An X-ray analyzer according to an aspect of the present invention includes an excitation source for exciting a sample to be analyzed and radiating a characteristic X-ray; an X-ray detector for detecting the characteristic X-ray; a collimator for regulating a range of the characteristic X-ray incident to the X-ray detector; at least one window for transmitting the characteristic X-ray between the sample and the X-ray detector; and a cooling unit for cooling the window such that a temperature of the window is lower than an atmospheric window, wherein the window includes an aluminum film and an insulating film laminated therein, wherein a total thickness of the aluminum film of the at least one window is equal to or greater than 150 nm and is less than 300 nm, and wherein the size of the collimator is set such that a quantity of radiant heat to the X-ray detector of the atmospheric temperature when the window is not present becomes equal to or less than 10 μW.

According to the X-ray analyzer of the aspect of (1), blackbody radiation from outside may be sufficiently lowered by the at least one window and the collimator and, as a result, the quantity of radiant heat applied to the X-ray detector may be lower than the caloric value of the X-ray detector, thereby stably operating the X-ray detector. In addition, the total thickness of the aluminum film of the at least one window may be reduced to the minimum and, as a result, an X-ray of 1 KeV or less is efficiently acquired.

In addition, when the total thickness of the aluminum film is less than 150 nm, blackbody radiation from outside cannot be sufficiently lowered. In addition, when the total thickness of the aluminum film becomes equal to or greater than 300 nm, transmission attenuation of the X-ray of 1 KeV or less increases to reduce efficiency. In addition, when the size of the collimator is set such that a quantity of radiant heat to the X-ray detector of the atmospheric temperature when the window is not present cannot become equal to or less than 10 μW, blackbody radiation from outside cannot be sufficiently lowered.

(2) In the X-ray analyzer of (1), the at least one window may include a first window and a second window, and a first cooling unit for cooling the first window such that a temperature of the first window is equal to or greater than 20K and is equal to or less than 50K and a second cooling unit for cooling the second window such that a temperature of the second window is equal to or greater than 1K and is equal to or less than 5K may be further included.

According to the X-ray analyzer according to the aspect of (2), by decreasing the temperature stepwise by the first window and the second window from the atmospheric temperature of the sample to be analyzed toward the X-ray detector, it is possible to prevent the temperature of the X-ray detector from rising by heat radiation to ensure a desired operation property.

In addition, when the temperature of the first window becomes higher than 50K, stepwise temperature reduction from the atmospheric temperature toward the X-ray detector cannot appropriately be achieved. In addition, in order to set the temperature of the first window to be less than 20K, the output necessary for the first cooling unit may become excessive. In addition, when the temperature of the second window becomes higher than 5K, the quantity of radiant heat applied to the X-ray detector cannot be sufficiently reduced. In addition, in order to set the temperature of the second window to be less than 20K, the output necessary for the second cooling unit may become excessive.

(3) In the X-ray analyzer of (2), the thickness of the aluminum film of the first window may be set to be equal to or greater than 100 nm.

According to the X-ray analyzer according to the aspect of (3), stepwise temperature reduction from the atmospheric temperature toward the X-ray detector may be appropriately achieved.

In addition, when the thickness of the aluminum film of the first window is less 100 nm, stepwise temperature reduction cannot be appropriately achieved.

(4) In the X-ray analyzer of (2) or (3), the at least one window may include a first window, a second window and a third window, and a third cooling unit for cooling the third window such that a temperature of the third window is equal to or less than 0.3K may be included.

According to the X-ray analyzer according to the aspect of (4), by decreasing the temperature stepwise by the first window, the second window and the third window from the atmospheric temperature of the sample to be analyzed toward the X-ray detector, it is possible to more stably prevent the temperature of the X-ray detector from rising by heat radiation and to more stably ensure a desired operation property.

(5) In the X-ray analyzer of any one of (1) to (4), the size of the collimator may be set to be 300 μm or less.

According to the X-ray analyzer according to the aspect of (5), it is possible to further shield influence of blackbody radiation of 5K or less.

In addition, when the size of the collimator becomes greater than 300 μm, it is impossible to efficiently shield influence of blackbody radiation of 5K or less.

(6) In the X-ray analyzer of any one of (1) to (5), the thickness of the insulating film may be set to be equal to or less than 100 nm.

According to the X-ray analyzer according to the aspect of (6), it is possible to appropriately hold the aluminum film while suppressing increase in transmission attenuation of the characteristic X-ray.

When the thickness of the insulating film becomes greater than 100 nm, transmission attenuation of the characteristic X-ray increases and efficiency decreases.

(7) In the X-ray analyzer of any one of (1) to (6), the insulating film may be formed of an organic film including at least one of polyimide and paraxylene-based polymer.

According to the X-ray analyzer according to the aspect of (7), it is possible to appropriately hold the aluminum film while suppressing increase in transmission attenuation of the characteristic X-ray.

(8) In the X-ray analyzer of any one of (1) to (6), the insulating film may be formed of a silicon material including silicon nitride or silicon.

According to the X-ray analyzer according to the aspect of (7), it is possible to appropriately hold the aluminum film while suppressing decrease in acquisition efficiency of characteristic X-ray of 1 keV or less. In addition, according to a silicon nitride film, since oxygen or carbon is not contained in the film, it is possible to appropriately analyze oxygen and carbon.

(9) In the X-ray analyzer of any one of (1) to (8), a through-hole formed portion in which a plurality of through-holes is formed may be included between the sample and the X-ray detector, and the size of each of the plurality of through-holes may be set to be 5 μm or less.

According to the X-ray analyzer according to the aspect of (9), since the wavelength of blackbody radiation of the atmospheric temperature (for example, 27° C. which is the room temperature) is about 10 μm, when the size of each of the plurality of through-holes is 5 μm or less, it is possible to more efficiently shield blackbody radiation.

In addition, when the size of each of the plurality of through-holes becomes greater than 5 μm, it is impossible to efficiently shield blackbody radiation.

(10) In the X-ray analyzer according to any one of (1) to (9), a pressure-resistant X-ray window mounted in a through-hole formed between the sample and the X-ray detector may be included in a housing for housing the at least one window and the X-ray detector.

Although a pressure difference is generated between the chamber for housing the sample and the X-ray detector housed in the housing, it is possible to stably operate the X-ray detector.

According to the aspects of the present invention, blackbody radiation from outside may be sufficiently lowered by at least one window and a collimator and, as a result, the quantity of radiant heat applied to the X-ray detector is lower than the caloric value of the X-ray detector, thereby stably operating the X-ray detector. In addition, the total thickness of the aluminum film of the at least one window may be reduced to the minimum and, as a result, the X-ray of 1 KeV or less may be efficiently acquired.

Hereinafter, an X-ray analyzer according to an embodiment of the present invention will be described with reference to the accompanying drawings.

The X-ray analyzer 10 of the present embodiment may be used as a composition analyzer such as an electron microscope, an ion microscope, an X-ray microscope, a fluorescent X-ray analyzer, for example.

Figure 1:
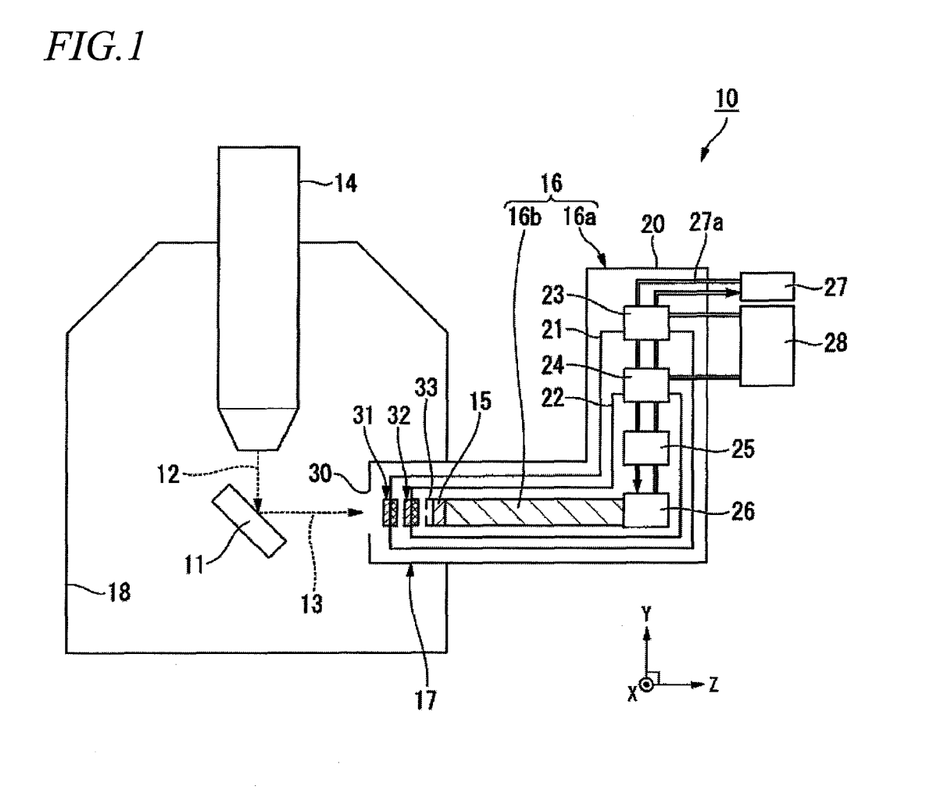
FIG. 1 is a cross-sectional view schematically showing the configuration of an X-ray analyzer according to an embodiment of the present invention.

As shown in FIG. 1, the X-ray analyzer 10 includes an electron gun 14 for irradiating an electron beam 12 to a sample 11 to be analyzed to excite the sample 11 and radiating a characteristic X-ray 13 from the sample 11 and a superconducting transition edge sensor (TES) 15 as an X-ray detector for detecting the characteristic X-ray 13 radiated from the sample 11.

The TES 15 uses superconducting transition of a superconductor and holds an operation point in the intermediate state of normal conduction and superconduction in the detection operation of the X-ray. When one X-ray is absorbed into the TES 15, in a state in which the operation point is held during superconducting transition, for example, resistance change of several mΩ is obtained with respect to temperature change of 100 µK, thereby obtaining a radiation pulse of the order of µA. By storing data for obtaining a relation between a pulse peak value and radiation in advance, even when radiation having unknown energy is irradiated to the TES 15, it is possible to detect the energy of the incident radiation from a signal pulse peak value.

The X-ray analyzer 10 includes a cooling unit 16 for cooling the TES 15.

The cooling unit 16 includes a refrigerator body 16a and a cold head 16b connected to a most cooled place of the refrigerator body 16a. The TES 15 is mounted on the front end of the cold head 16b placed in a snout 17 having a heat insulation structure mounted in the refrigerator body 16a.

The sample 11, the electron gun 14 and the front end of the snout 17 are placed in a chamber 18 such that the insides of the snout 17 and the chamber 18 are evacuated by a turbo molecule pump, a diffusion pump or the like and a vacuum degree is about $10^{-3}$ to $10^{-5}$ Pa.

The refrigerator body 16a is a dilution refrigerator or an insulated demagnetized refrigerator, for example. The dilution refrigerator performs cooling using an enthalpy difference when 3 He is dissolved from a rich phase to a poor phase within the mixing chamber. The insulated demagnetized refrigerator cools an object connected to a magnetic material by applying a magnetic field to the magnetic material to place a spin direction and increasing entropy when removing the magnetic field.

For example, the refrigerator body 16a which is a dilution refrigerator includes an outer surrounding shield 20, a first heat shield 21, a second heat shield 22, a first pot 23, a second pot 24, a fractional distillation device (still) 25, a mixer (mixing chamber) 26, a gas circulator 27 and a preliminary cooler 28.

The portions of the outer surrounding shield 20, the first heat shield 21 and the second heat shield 22 extend to cover the cold head 16b, thereby configuring the snout 17.

The first heat shield 21 is housed in the outer surrounding shield 20. The second heat shield 22 is housed in the first heat shield 21.

In the embodiment, the outer surrounding shield 20 serves as a housing that accommodates a first X-ray window 31, a second X-ray window 32 (which will be described later) and the TES 15.

The first pot 23 is formed in the first heat shield 21 inside the outer surrounding shield 20. The second pot 24 is formed in the second heat shield 22 inside the first heat shield 21. The fractional distillation device 25 and the mixer 26 are housed in the second heat shield 22. The cold head 16b is connected to the mixer 26.

The gas circulator 27 is placed outside the outer surrounding shield 20. The gas circulator 27 is connected to a gas circulation flow passage 27a placed inside the outer surrounding shield 20 to circulate 3 He in the gas circulation flow passage 27a. The first pot 23, the second pot 24, the fractional distillation device 25 and the mixer 26 are connected to the gas circulation flow passage 27a.

The preliminary cooler 28 is placed outside the outer surrounding shield 20. The preliminary cooler 28 is connected to the first pot 23 and the second pot 24. The preliminary cooler 28 is a mechanical refrigerator such as a GM refrigerator, for example.

The first pot 23 is cooled to about 20 K, for example, by the preliminary cooler 28. The first pot 23 cools the first heat shield 21.

The second pot 24 is cooled to about 1 K, for example, by the preliminary cooler 28. The second pot 24 cools the second heat shield 22.

The first pot 23 and the second pot 24 liquefy 3 He of the gas circulation flow passage 27a.

The fractional distillation device 25 evaporates (fractionates) 3 He in the poor phase. The fractional distillation device 25 is maintained at about 0.7 K less than 1 K, for example.

The mixer 26 moves 3 He from the rich phase to the poor phase. The mixer 26 is maintained at about 100 mK, for example. The mixer 26 cools the cold head 16b up to about 100 mK.

The temperature of the outer surrounding shield 20 is an atmospheric temperature (for example, 27° C. which is a room temperature).

Figure 2:
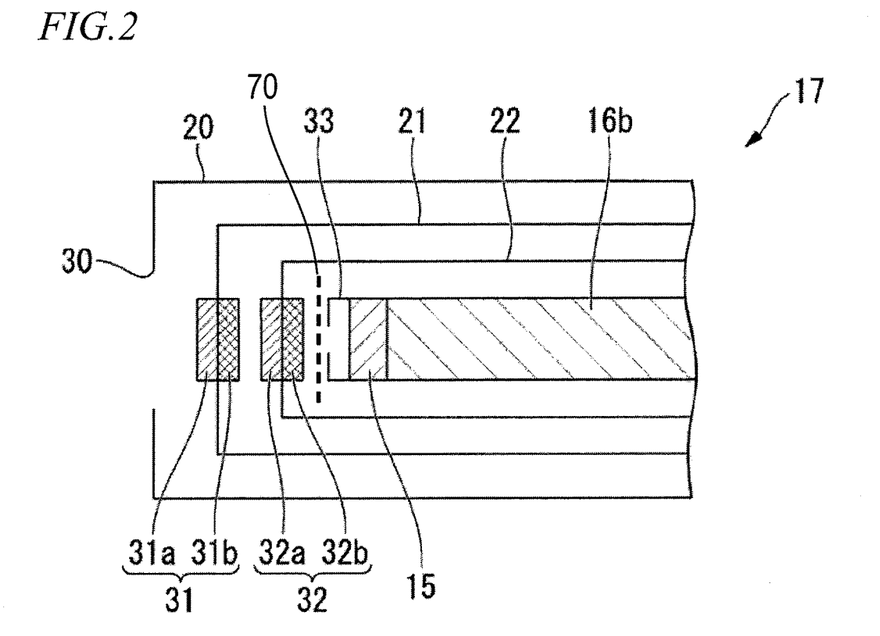
FIG. 2 is a cross-sectional view schematically showing the configuration of the snout in an X-ray analyzer according to the embodiment of the present invention.

As shown in FIG. 2, in the snout 17, the outer surrounding shield 20 includes a front end having formed therein a through-hole 30 through which the characteristic X-ray 13 radiated from the sample 11 passes toward the TES 15.

In the snout 17, the first heat shield 21 is provided between the outer surrounding shield 20 and the second heat shield 22. The first heat shield 21 includes a first X-ray window 31 for enabling the characteristic X-ray 13 radiated from the sample 11 to reach the TES 15. The first X-ray window 31 includes an aluminum film 31a and an insulating film 31 laminated therein.

In the snout 17, the second heat shield 22 is provided between the first heat shield 21 and the cold head 16b. The second heat shield 22 includes a second X-ray window 32 for enabling the characteristic X-ray 13 radiated from the sample 11 to reach the TES 15. The second X-ray window 32' includes an aluminum film 32a and an insulating film 32b laminated therein.

In the snout 17, the first heat shield 21 and the second heat shield 22 transmit the characteristic X-ray 13 radiated from the sample 11 to the cold head 16b and shield heat radiation from outer surrounding shield 20.

Although, in the snout 17 shown in FIG. 2, the insulating films 31b and 32b are provided at the side of the TES 15 rather than the aluminum films 31a and 32a, the aluminum films 31 a and 32a may be provided at the side of the TES 15 rather than the insulating films 31b and 32b.

A collimator 33 is formed in front of the TES 15 in a direction from the sample 11 to the TES 15 (for example, a Z direction). The collimator 33 restricts the heat intruded from outside to the TES 15 and irradiates the characteristic X-ray 13 to only some areas of the TES 15.

Figure 3:
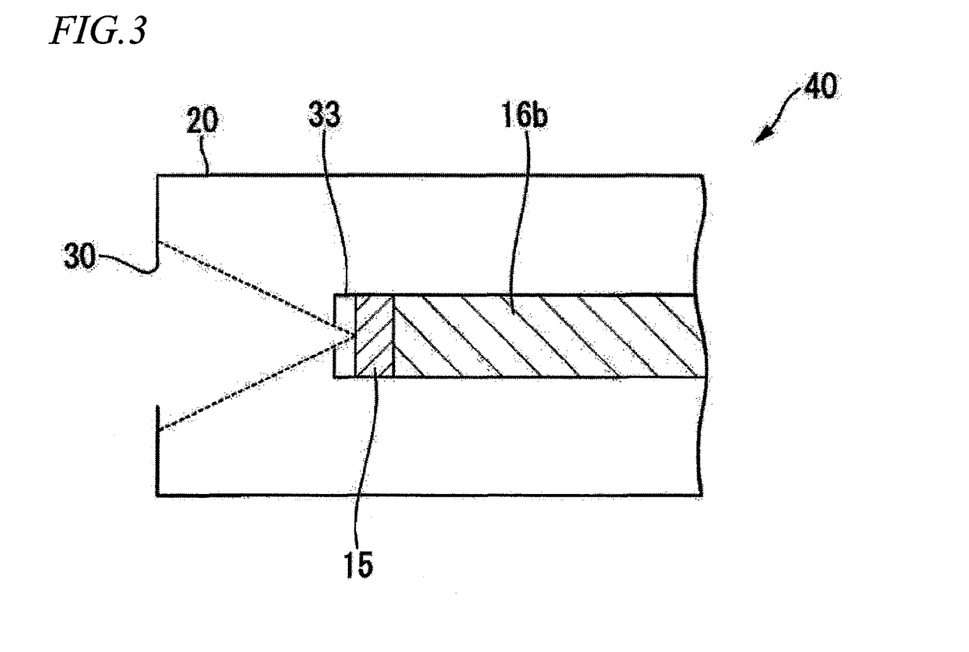
FIG. 3 is a cross-sectional view schematically showing the configuration of a snout according to a comparative example of the present invention.

Hereinafter, as a comparative example of the embodiment, the case in which the first X-ray window 31 and the second X-ray window 32 are not present between the sample 11 and the collimator 33 in the snout 17 will be described. FIG. 3 is a cross-sectional view schematically showing the configuration of a snout 40 according to a comparative example.

When the first X-ray window 31 and the second X-ray window 32 are not present, electromagnetic waves by blackbody radiation from the room temperature pass through the collimator 33 to intrude into the TES 15. Although the operation point of the TES 15 is held by heat balance shown in Equation (1), heat Pex intruded from outside should be sufficiently lower than the calorific value of the TES 15. For example, the self-calorific value when the current of the TES 15 is 50 µA and operation resistance is 30 mΩ is 75 pW. When the operation point of the TES 15 is changed by change in the heat Pex intruded from outside, energy resolution may deteriorate and thus the heat Pex intruded from outside is preferably set to 0.1 pW or less. When the first X-ray window 31 and the second X-ray window 32 are not present, the TES 15 directly views the outer surrounding shield 20. When the size (for example, the diameter) of the aperture of the collimator 33 is 0.2 mm and the distance between the collimator 33 and the TES 15 is 0.3 mm, the size (for example, the diameter) of the area of the outer surrounding shield 20 when the outer surrounding shield 20 is viewed from the TES 15 becomes 6.6 mm.

Heat radiation Q from outer surrounding shield 20 to the cold head 16b is described as shown in Equation (2) below, for example, based on a Stefan-Boltzman constant $\sigma$ (=5.67 W/(m$^2$·K$^4$))), the area S1 of the outer surrounding shield 20, the area S2 of the TES 15 viewing the outer surrounding shield 20 via the collimator 33, emissivity $\varepsilon_1$ of the outer surrounding shield 20, emissivity $\varepsilon_2$ of the front end of the cold head 16b, the temperatures $T_1$ and $T_2$ of the TES 15 and the outer surrounding shield 20.

$$Q = \sigma(T_1^4 - T_2^4)S1 \times \frac{1}{\frac{1}{\varepsilon_1} + \frac{S2}{S1}\left(\frac{1}{\varepsilon_2} - 1\right)} \quad (2)$$

In Equation (2), when emissivity $\varepsilon_1$ is 0.9 on the assumption that the reflectivity of the outer surrounding shield 20 is bad and emissivity $\varepsilon_2$ is 0.1 on the assumption that the reflectivity of the cold head 16b is good, the heat radiation Q from outer surrounding shield 20 to the front end of the cold head 16b becomes 1.8 μW. Since this calculated result is ideal, actually, a larger value, for example, about Q=10 μW may be assumed.

Hereinafter, the first X-ray window 31 and the second X-ray window 32 of the embodiment will be described.

In order to stably operate the TES 15, since the heat Pex intruded from outside is preferably set to 0.1 pW or less, blackbody radiation from outer surrounding shield 20 needs to be reduced by 7 digits or more by the first X-ray window 31 and the second X-ray window 32.

Figure 4:
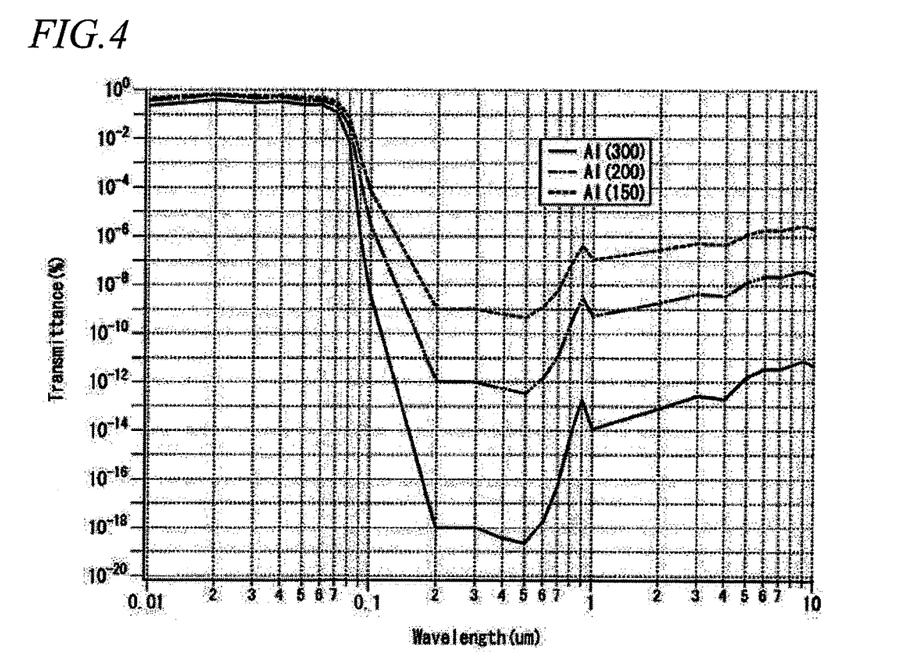
FIG. 4 is a diagram showing an example of a relation between the wavelength and transmittance of an X-ray transmitting an aluminum film and the thickness of an aluminum film according to the embodiment of the present invention.

FIG. 4 is a diagram showing the transmission property of the X-ray when the total thicknesses of all aluminum films 31a and 32a of the first X-ray window 31 and the second X-ray window 32 are respectively 150 nm, 200 nm and 300 nm.

When blackbody radiation of the atmospheric temperature (for example, 27° C. which is the room temperature) is converted into a wavelength, about 10 μm is obtained.

With respect to a Planck constant h, a speed of light c, a wavelength $\lambda$, a Boltzman constant $k_B$ and a temperature T, there is a relation of hc/$\lambda$=$k_B$·T. To this end, in order to reduce the transmission property in the vicinity of the wavelength of 10 μm by 7 digits or more, at least the thickness of the aluminum film needs to be 200 nm or more.

By using an appropriate temperature range as the atmospheric temperature, the required thickness of the aluminum film is equal to or greater than 150 nm and is less than 300 nm.

Since the first X-ray window 31 is cooled to the same temperature as the first heat shield 21, when the temperature of the first heat shield 21 is T1, the first X-ray window 31 influences blackbody radiation of the temperature T1. Blackbody radiation when the temperature T1 of the first X-ray window 31 is 20 K to 50K is 36 pW to 1.4 nW (wavelength: 60 μm to 150 μm).

Since the second X-ray window 32 is cooled to the same temperature as the second heat shield 22, when the temperature of the second heat shield is T2, the second X-ray window 32 influences blackbody radiation of the temperature T2. Blackbody radiation when the temperature T2 of the second X-ray window 32 is 1 K to 5K is 0.0002 pW to 0.14 pW (wavelength: 600 μm to 3 mm). The second X-ray window 32 may obtain target radiant heat because blackbody of the temperature T2 influences the TES 15.

Since the thickness of the aluminum film between the outer surrounding shield 20 of the atmospheric temperature to the TES 15 is preferably 200 nm or more, for example, the thickness of the aluminum film 31a of the first X-ray window 31 is 100 nm and the thickness of the aluminum film 32a of the second X-ray window 32 is 100 nm.

In addition, by setting the thickness of the aluminum film 31a of the first X-ray window 31 to 100 nm or more, it is possible to decrease reduction of blackbody radiation necessary for the second X-ray window 32 to improve stability in operation of the TES 15.

According to the size D of the aperture of the collimator 33 and the wavelength X of the electromagnetic wave incident to the collimator 33, from the principle of wavelength limit, it is known that the electromagnetic wave having a wavelength greater than D=$\lambda$/2 does not pass through the aperture. Since the wavelength when the temperature T2 of the second X-ray window 32 is 5K is 600 μm, when the size of the aperture of the collimator 33 is equal to or less than 300 μm, influence of blackbody radiation of 5K or less may be further shielded.

In addition, when the size of the aperture of the collimator 33 is 75 μm, blackbody radiation from 50K may be shielded to thermally stably operate the TES 15.

It is preferable to set the aperture size (size of aperture) of the collimator 33 to be 10 μm or larger so that the collimator 33 and the TES 15 may be aligned with decent accuracy with no difficulty. The insulating films 31b and 32b of the first X-ray window 31 and the second X-ray window 32 are used to hold the aluminum films 31a and 32a, but contribute to attenuation of the characteristic X-ray 13 and thus are as thin as possible to the extent that the insulating films are not damaged as a structure. The insulating films 31b and 32b are preferably composed of elements considering transmittance of the characteristic X-ray 13 and an organic material including at least one of polyimide and paraxylene-based polymer or a silicon material including silicon nitride or silicon may be used. From the viewpoint of X-ray transmittance, the thicknesses of the insulating films 31b and 32b are preferably equal to or less than 100 nm.

It is preferable to set the thicknesses of the insulating films 31b and 32b to be 10 nm or more so as to obtain a decent physical strength as a supporting layer.

As described above, according to the X-ray analyzer 10 of the present embodiment, blackbody radiation from outside may be sufficiently lowered by the first X-ray window 31, the second X-ray window 32 and the collimator 33. Since the radiant heat applied to the TES 15 may be less than the caloric value, it is possible to stably operate the TES 15. In addition, the total thickness of the aluminum films 31a and 32a in the first X-ray window 31 and the second X-ray window 32 may be reduced to the minimum and, as a result, the characteristic X-ray 13 of 1 keV or less may be efficiently acquired.

When the total thickness of the aluminum films 31a and 32a are reduced to less than 150 nm, blackbody radiation from outside may not be sufficiently lowered. When the total thickness of the aluminum films 31a and 32a increases to 300 nm or more, transmission attenuation of the characteristic X-ray 13 of 1 keV or less increases and efficiency decreases.

When the size of the collimator 33 is set such that a quantity of radiant heat to the TES 15 of the atmospheric temperature when the first X-ray window 31 and the second X-ray window 32 are not present cannot become equal to or less than 10 μW, blackbody radiation from outside may not be sufficiently lowered.

By decreasing the temperature stepwise by the first X-ray window 31 and the second X-ray window 32 from the atmospheric temperature of the sample 11 to be analyzed toward the TES 15, the temperature of the TES 15 is prevented from rising by heat radiation to ensure a desired operation property.

When the temperature of the first X-ray window 31 becomes higher than 50K, stepwise temperature reduction from the atmospheric temperature toward the TES 15 may not appropriately be achieved. In order to set the temperature of the first X-ray window 31 to be less than 20K, the output necessary for the first pot 23 may become excessive.

When the temperature of the second X-ray window 32 becomes higher than 5K, the quantity of radiant heat applied to the TES 15 cannot be sufficiently reduced. In addition, in order to set the temperature of the second X-ray window 32 to be less than 20K, the output necessary for the second pot 24 may become excessive.

Since the size of the aperture of the collimator 33 is 300 μm or less, it is possible to further shield influence of blackbody radiation of 5K or less with respect to the TES 15.

When the size of the collimator 33 becomes greater than 300 μm, it is impossible to efficiently shield influence of blackbody radiation of 5K or less.

Since the thicknesses of the insulating films 31b and 32b are 100 nm or less, it is possible to appropriately hold the aluminum films 31a and 32a while suppressing increase in transmission attenuation of the characteristic X-ray 13.

When the thicknesses of the insulating films 31b and 32b become greater than 100 nm, transmission attenuation of the characteristic X-ray increases and efficiency decreases.

When the insulating films 31b and 32b are formed of an organic material including at least one of polyimide and a paraxylene based polymer, it is possible to appropriately hold the aluminum films 31a and 32a while suppressing increase in transmission attenuation of the characteristic X-ray 13. When the insulating films 31b and 32b are formed of a silicon material including silicon nitride or silicon, it is possible to appropriately hold the aluminum films 31a and 32a while suppressing decrease in acquisition efficiency of characteristic X-ray of 1 keV or less. According to a silicon nitride film, since oxygen or carbon is not contained in the film, it is possible to appropriately analyze oxygen and carbon.

Hereinafter, a first modified example of the above-described embodiment will be described.

Although, in the above-described embodiment, the X-ray analyzer 10 includes two X-ray windows, that is, the first X-ray window 31 and the second X-ray window 32, the present invention is not limited thereto.

Figure 5:
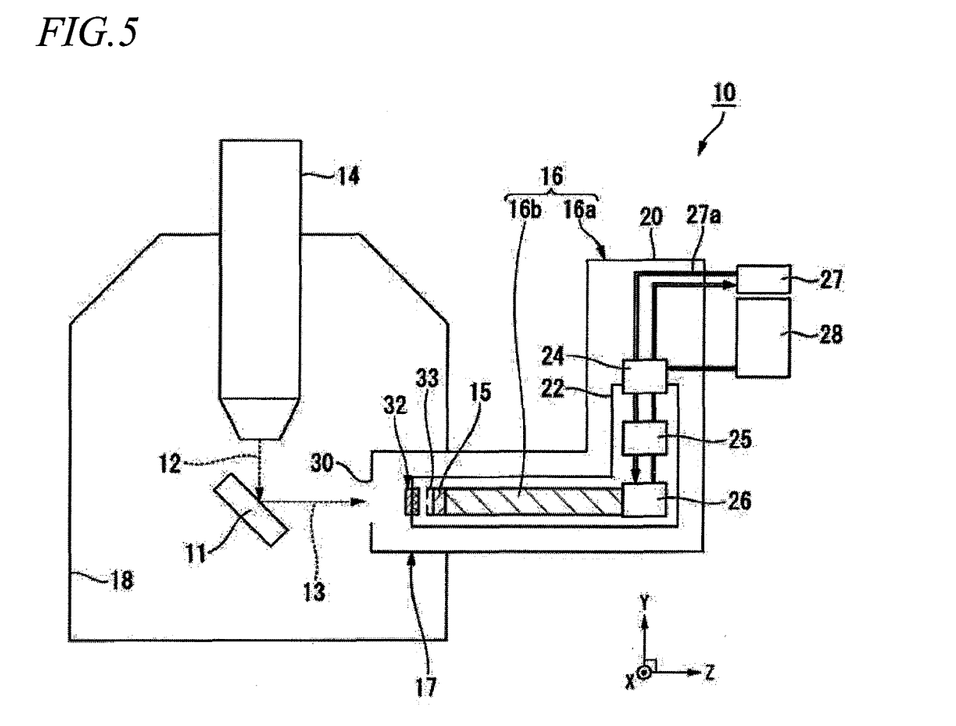
FIG. 5 is a cross-sectional view schematically showing the configuration of an X-ray analyzer according to a first modified example of the embodiment of the present invention.
Figure 6:
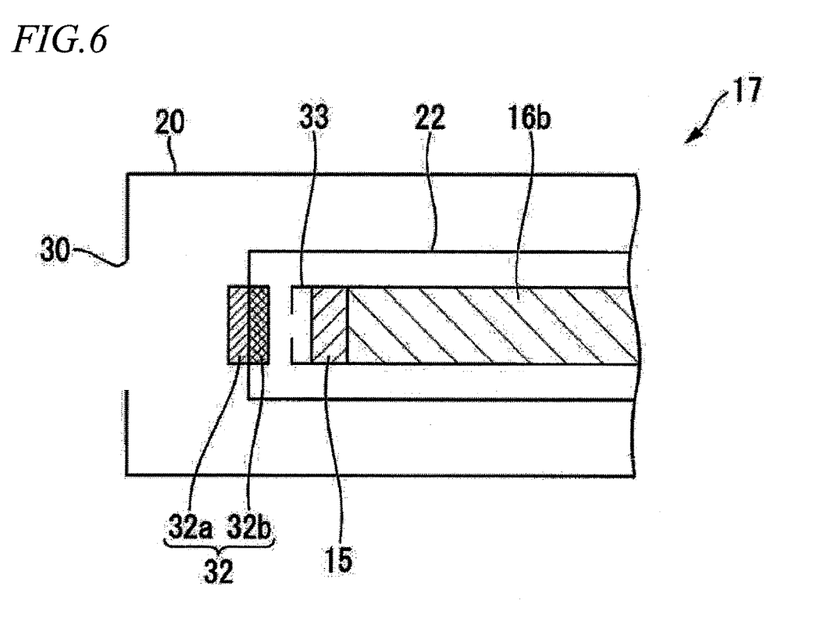
FIG. 6 is a cross-sectional view schematically showing the configuration of a snout in the X-ray analyzer according to the first modified example of the embodiment of the present invention.

In the X-ray analyzer 10 according to the first modified example of the above-described embodiment, as shown in FIGS. 5 and 6, the first X-ray window 31 of the X-ray analyzer 10 of the above-described embodiment is omitted.

The configuration of the X-ray analyzer 10 according to the first modified example is different from that of the X-ray analyzer 10 of the above-described embodiment in that the X-ray analyzer 10 according to the first modified example does not include the first heat shield 21, the first pot 23 and the first X-ray window 31.

In the X-ray analyzer 10 according to the first modified example, the thickness of the aluminum 32a of the second X-ray window 32 is equal to or greater than 150 and is less than 300 nm. The thickness of the aluminum film 32a of the second X-ray window 32 is more preferably 200 nm. The thickness of the aluminum film 32b of the second X-ray window 32 is preferably 100 nm or less. The temperature T2 of the second X-ray window 32 cooled to the same temperature as the second heat shield 22 is 1K to 5K. According to the first modified example, when the cooling output of the second pot 24 is sufficient to maintain the temperature T2 of the second X-ray window 32 at 1K to 5K, it is possible to simplify the configuration of the X-ray analyzer 10 while thermally stably operate the TES 15.

Hereinafter, a second modified example of the above-described embodiment will be described.

Although, in the above-described embodiment, the X-ray analyzer 10 includes two X-ray windows, that is, the first X-ray window 31 and the second X-ray window 32, the present invention is not limited thereto. More than two (for example, 3) X-ray windows may be included.

Figure 7:
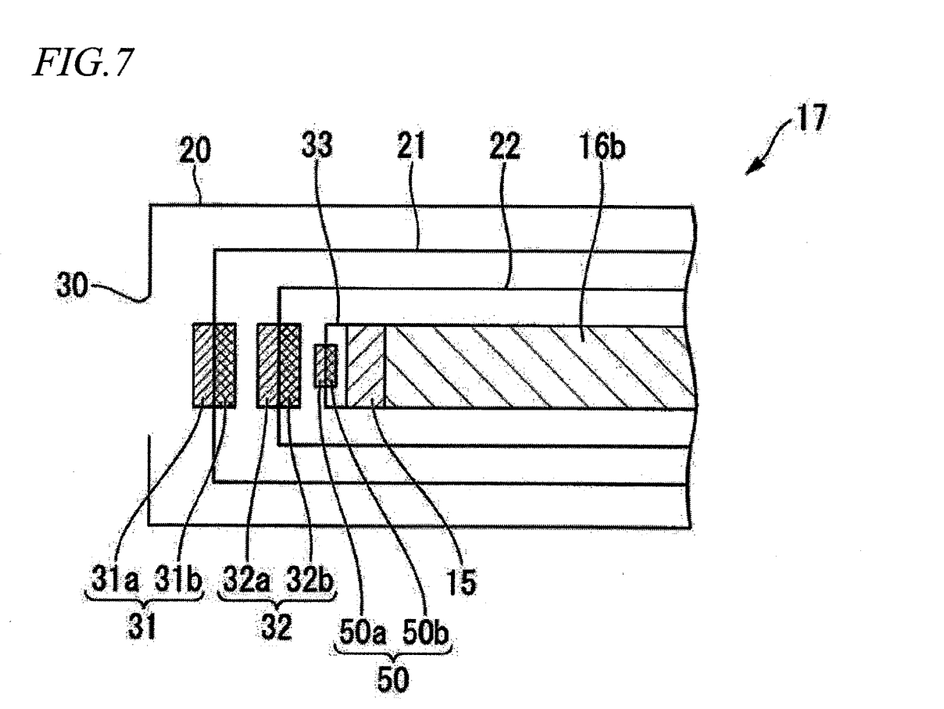
FIG. 7 is a cross-sectional view schematically showing the configuration of a snout in an X-ray analyzer according to a second modified example of the embodiment of the present invention.

In the X-ray analyzer 10 according to the second modified example of the above-described embodiment, as shown in FIG. 7, in addition to the first X-ray window 31 and the second X-ray window 32 of the X-ray analyzer 10 of the above-described embodiment, a third X-ray window 50 is included.

The configuration of the X-ray analyzer 10 according to the second modified example is different from that of the X-ray analyzer 10 of the above-described embodiment in that the X-ray analyzer 10 according to the second modified example includes the third X-ray window 50.

In the X-ray analyzer 10 according to the second modified example, the third X-ray window 50 includes an aluminum film 50a and insulating film 50b laminated therein. In addition, although, in the snout 17 shown in FIG. 7, the insulating film 50b is located at the side of the TES 15 rather than the insulating film 50a, the aluminum film 50a may be located at the side of the TES 15 rather than the insulating film 50b.

Since the thickness of the aluminum film is preferably 200 nm or more from outside surrounding field 20 of the atmospheric temperature to the TES 15, the total thickness of the aluminum films 31a, 32a and 50a of the first X-ray window 31, the second X-ray window 32 and the third X-ray window 50 is equal to or greater than 150 nm and is less than 300 nm and is more preferably 200 nm.

The temperature of the third X-ray window 50 cooled by the cold head 16b is set to 0.3 K or less.

According to the second modified example, by decreasing the temperature stepwise by the first X-ray window 31, the second X-ray window 32 and the third X-ray window 50 from the atmospheric temperature of the sample 11 to be analyzed toward the TES 15, it is possible to more stably prevent the temperature of the TES 15 from rising by heat radiation and to more stably ensure a desired operation property.

Hereinafter, other modified examples will be described.

In the above-described embodiment, the X-ray analyzer 10 may include a through-hole formed portion 70, such as a metal mesh having a plurality of through-holes formed therein between the sample 11 and the TES 15, as shown in FIG. 2.

Since the wavelength of blackbody radiation of the atmospheric temperature (for example, 27° C. which is the room temperature) is about 10 μm, when the size of each of the plurality of through-holes is 5 µm or less, it is possible to more efficiently shield blackbody radiation.

It is preferable to set the size of each of the plurality of through-holes to be 1 µm or more so as to ensure the dimensional accuracy of each through-holes.

Although, in the above-described embodiment, the collimator 33 is formed in the TES 15, the present invention is not limited thereto and the collimator 33 may be fixed to the cold head 16b.

Figure 8:
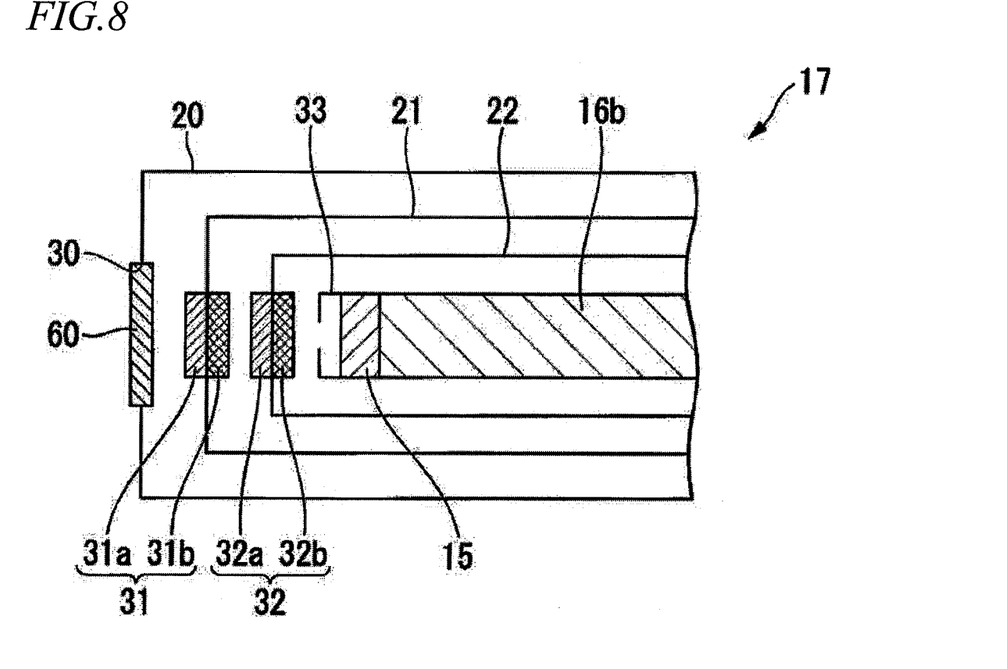
FIG. 8 is a cross-sectional view schematically showing the configuration of a snout in an X-ray analyzer according to another modified example of the embodiment of the present invention.

In the above-described embodiment, as shown in FIG. 8, a pressure-resistant X-ray window 60 may be provided in the through-hole 30. As the pressure-resistant X-ray window 60, for example, an organic material including at least one of polyimide and paraxylene-based polymer may be used. Although a pressure difference is generated between the chamber 18 for housing the sample 11 and the TES 15 housed in the snout 17, it is possible to stably operate the TES 15.

The technical range of the present invention is not limited to the above-described embodiments and includes various modifications of the above-described embodiments without departing from the scope of the present invention. That is, the configuration of the above-described embodiments are merely exemplary and may be appropriately changed.

What is claimed is:

1. An X-ray analyzer comprising:
   an excitation source for exciting a sample to be analyzed to radiate a characteristic X-ray;
   an X-ray detector that detects the characteristic X-ray;
   a collimator that regulates a range of the characteristic X-ray incident to the X-ray detector;
   at least one window that is provided between the sample and the X-ray detector and allows the characteristic X-ray to pass through; and
   a cooling unit that cools the window to a temperature that is lower than an atmospheric temperature,
   wherein the window is laminated with one or more layers of an aluminum film and one or more layers of an insulating film,
   wherein a total thickness of the aluminum film of the at least one window is equal to or greater than 150 nm and is less than 300 nm, and
   wherein a size of an aperture of the collimator is 300 µm or less.

2. The X-ray analyzer according to claim 1,
   wherein the at least one window includes a first window and a second window, and
   wherein the cooling unit includes a first cooling unit that cools the first window to a temperature that is equal to or greater than 20K and is equal to or less than 50K and a second cooling unit that cools the second window to a temperature that is equal to or greater than 1K and is equal to or less than 5K.

3. The X-ray analyzer according to claim 2,
   wherein a thickness of the aluminum film of the first window is equal to or greater than 100 nm.

4. The X-ray analyzer according to claim 2,
   wherein the at least one window further includes a third window, and
   wherein the cooling unit further includes a third cooling unit that cools the third window to a temperature that is equal to or less than 0.3K.

5. The X-ray analyzer according to claim 1,
   wherein the thickness of the insulating film is equal to or less than 100 nm.

6. The X-ray analyzer according to claim 1,
   wherein the insulating film is formed of an organic film including at least one of polymide and paraxylene-based polymer.

7. The X-ray analyzer according to claim 1,
   wherein the insulating film is formed of a silicon material including silicon nitride or silicon.

8. The X-ray analyzer according to claim 1 further comprising:
   a through-hole formed portion, in which a plurality of through-holes are formed, is provided between the sample and the X-ray detector,
   wherein a size of each of the plurality of through-holes 5 µm or less.

9. The X-ray analyzer according to claim 1 further comprising:
   a housing that accommodates the at least one window and the X-ray detector; and
   a pressure-resistant X-ray window that is mounted in a through-hole formed on the housing at a position between the sample and the X-ray detector.

* * * * *